(12) United States Patent
Abolfathi et al.

(10) Patent No.: US 7,878,801 B2
(45) Date of Patent: *Feb. 1, 2011

(54) SYSTEMS AND METHODS FOR DENTAL APPLIANCE COMPLIANCE INDICATION

(75) Inventors: Amir Abolfathi, Woodside, CA (US); Jennifer C. Chen, San Francisco, CA (US); Chunhua Li, Cupertino, CA (US); Robert E. Tricca, Danville, CA (US); Benjamin M. Wu, San Marino, CA (US); Eric E. Kuo, Foster City, CA (US); Loc X. Phan, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 9 days.

This patent is subject to a terminal disclaimer.

(21) Appl. No.: 12/250,879

(22) Filed: Oct. 14, 2008

(65) Prior Publication Data

US 2009/0117507 A1 May 7, 2009

Related U.S. Application Data

(63) Continuation-in-part of application No. 10/949,717, filed on Sep. 24, 2004, now Pat. No. 7,553,157, and a continuation-in-part of application No. 11/745,211, filed on May 7, 2007, now abandoned.

(51) Int. Cl.
*A61C 3/00* (2006.01)

(52) U.S. Cl. .................................................. 433/6
(58) Field of Classification Search ............ 433/6, 433/24

See application file for complete search history.

(56) References Cited

U.S. PATENT DOCUMENTS

| 3,192,302 | A |   | 6/1965  | Keefer          |        |
|-----------|---|---|---------|-----------------|--------|
| 3,503,127 | A |   | 3/1970  | Kasdin et al.   |        |
| 3,555,386 | A |   | 1/1971  | Wisman          |        |
| 3,564,205 | A |   | 2/1971  | Tyler           |        |
| 3,813,781 | A | * | 6/1974  | Forgione        | 433/68 |
| 4,072,268 | A |   | 2/1978  | Perris          |        |
| 4,124,793 | A |   | 11/1978 | Colman          |        |

(Continued)

FOREIGN PATENT DOCUMENTS

DE 41 23 352 A1 1/1993

(Continued)

OTHER PUBLICATIONS

Jablonski, Illustrated Dictionary of Dentistry, W.B. Saunders Company, ISBN 0-7216-5055-4, pp. 678-680, copyright 1982.*

*Primary Examiner*—Ralph A Lewis

(74) *Attorney, Agent, or Firm*—Brooks, Cameron & Huebsch, PLLC

(57) ABSTRACT

An apparatus for monitoring orthodontic treatment compliance includes an appliance adapted to be worn over one or more teeth; and a compliance indicator mounted on the appliance to indicate compliance.

16 Claims, 9 Drawing Sheets

U.S. PATENT DOCUMENTS

| | | | |
|---|---|---|---|
| 4,192,456 A | 3/1980 | Shields et al. | |
| 4,310,047 A | 1/1982 | Branson | |
| 4,741,700 A * | 5/1988 | Barabe | 433/229 |
| 4,968,251 A | 11/1990 | Darnell | |
| 5,074,786 A | 12/1991 | Woodward | |
| 5,076,791 A | 12/1991 | Madray, Jr. | |
| 5,137,449 A | 8/1992 | Goldin et al. | |
| 5,194,003 A | 3/1993 | Garay et al. | |
| 5,326,685 A | 7/1994 | Gaglio et al. | |
| 5,437,872 A | 8/1995 | Lee | |
| 5,575,654 A | 11/1996 | Fontenot | |
| 5,575,655 A | 11/1996 | Darnell | |
| 5,587,520 A | 12/1996 | Rhodes | |
| 5,645,420 A * | 7/1997 | Bergersen | 433/6 |
| 5,993,413 A | 11/1999 | Aaltonen et al. | |
| 6,142,780 A | 11/2000 | Burgio | |
| 6,607,382 B1 | 8/2003 | Kuo et al. | |
| 6,813,131 B2 | 11/2004 | Schmalz | |
| 6,935,572 B1 | 8/2005 | Smole | |
| 7,553,157 B2 * | 6/2009 | Abolfathi et al. | 433/6 |
| 2006/0166157 A1 * | 7/2006 | Rahman et al. | 433/6 |
| 2008/0118882 A1 * | 5/2008 | Su | 433/2 |

FOREIGN PATENT DOCUMENTS

| | | |
|---|---|---|
| GB | 529805 | 11/1940 |
| GB | 710764 | 6/1954 |
| GB | 761565 | 11/1956 |
| GB | 905213 | 9/1962 |
| GB | 1274283 | 5/1972 |

* cited by examiner

SYSTEMS AND METHODS FOR DENTAL APPLIANCE COMPLIANCE INDICATION

PRIORITY INFORMATION

This application is a Continuation-in-Part of U.S. patent application Ser. No. 10/949,717 filed Sep. 24, 2004 now U.S. Pat. No. 7,553,157, and a Continuation in Part of U.S. patent application Ser. No. 11/745,211 filed May 7, 2007 now abandoned, the specifications of which are incorporated herein by reference.

BACKGROUND

The present invention is related to systems and methods for dental appliance compliance indication.

As noted in commonly owned U.S. Pat. No. 6,607,382 entitled "Methods and systems for concurrent tooth repositioning and substance delivery," the content of which is incorporated herewith, the repositioning of teeth may be accomplished with the use of a series of removable elastic positioning appliances such as the Invisalign® system available from Align Technology, Inc., the assignee of the present invention. Such appliances have a thin shell of elastic material that generally conforms to a patient's teeth but is slightly out of alignment with an initial or immediately prior tooth configuration. Placement of the elastic positioner over the teeth applies controlled forces in specific locations to gradually move the teeth into the new configuration. Repetition of this process with successive appliances comprising new configurations eventually moves the teeth through a series of intermediate configurations or alignment patterns to a final desired configuration. A full description of an exemplary elastic polymeric positioning appliance is described in U.S. Pat. No. 5,975,893, and in published PCT application WO 98/58596, the content of these documents are incorporated by reference for all purposes.

The appliance is effective in repositioning teeth when it is placed over the patients teeth. Although easy and convenient to wear, the patient may not wear the appliance as prescribed by the doctor or orthodontist. Extended removal of the appliance, for any reason beyond what is recommended, interrupts the treatment plan and lengthens the overall period of treatment. Since the appliance is removable by the patient, the doctor has to rely on the patient to comply with the prescription.

SUMMARY

Figure 1:
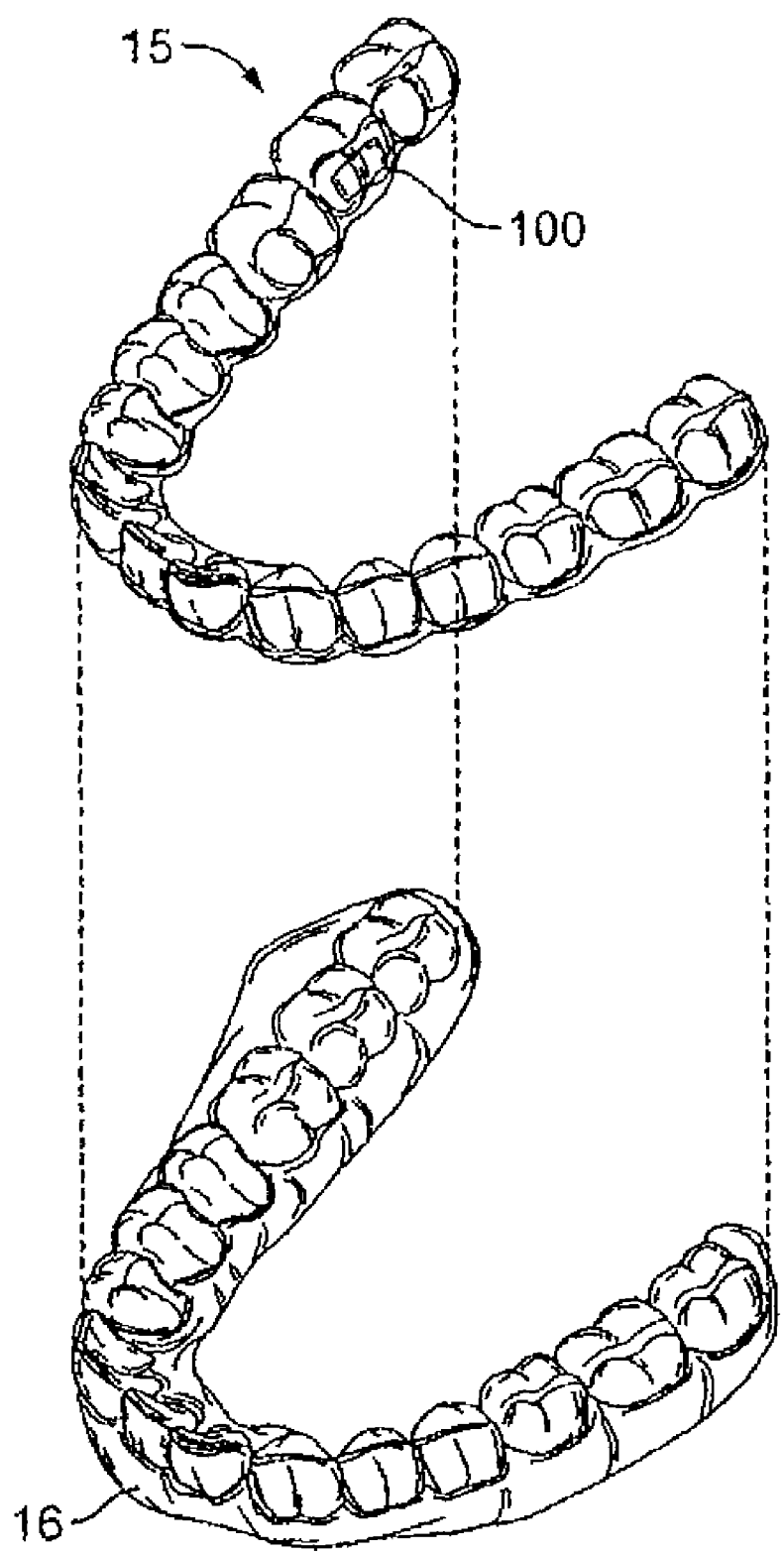
FIG. 1 shows an exemplary compliance indicator.

An apparatus for monitoring orthodontic treatment compliance includes an appliance adapted to be worn over one or more teeth; and a compliance indicator mounted on the appliance or teeth to indicate compliance.

Advantages of the system include one or more of the following. The apparatus provides better data for communicating device compliance with patients, including: increased patient knowledge and recall of appliance usage; increased compliance in wearing the dental appliance, and increased patient satisfaction as a result. The apparatus provides a channel of self-monitoring for the patient. The apparatus also reduces patient's anxiety levels without requiring verbal or written instructions since device usage is self-evident. The doctor or orthodontist also has better information on patient progress during the treatment.

The present invention provides devices, systems and methods for orthodontic treatment using repositioning appliances, typically elastic polymeric shells, while concurrently delivering substances to the teeth or gums, for example, to provide dental and periodontal and/or cosmetic therapies. Such therapies are traditionally provided with the use of a variety of accessories and devices which are applied using separate appliances, materials, etc. The present invention eliminates the need for such additional devices by incorporating these therapies into the repositioning appliance. Moreover, the ability to deliver therapeutic and other agents is concurrent with the course of a repositioning procedure.

By "concurrent" or "concurrently," it is meant that the substance or agent delivery to the teeth occurs during at least a portion of the duration of the repositioning of the teeth. Thus, the substance may be delivered continuously during the entire duration of the repositioning process, i.e. the substance may be present in or on each repositioning appliance in an amount or amounts sufficient to assure that it is released to the oral environment at all times the appliance is placed over the teeth. Alternatively, the substance may be present in or on the repositioning appliances at only selected times or over selected time intervals so that the substances are delivered at spaced-apart times during the repositioning process. For example, each successive repositioning appliance may be preloaded with a bolus of the substance so that the bolus is delivered to the patient at the outset of use of each new appliance. After the initial bolus is depleted, the substance will not be delivered again until the next successive appliance is used. As an alternative example, the patient could apply an amount of a substance at a time each day, where the substance is then released over a relatively short time interval and no more substance delivered until the next day. A multitude of other particular patterns are also possible.

While the appliances will be particularly intended for repositioning teeth, most often when used in systems of multiple aligners, they may in some instances be useful as drug or substance delivery devices without the concurrent repositioning of teeth. In particular, many of the specific device constructions described below are themselves novel and useful for substance delivery, and the present invention encompasses such devices.

In a first aspect of the present invention, an oral delivery appliance comprises an elastic repositioning appliance providing one or more substances or agents for oral delivery. As previously described, elastic repositioning appliances comprise a thin shell of elastic polymeric material having cavities shaped to receive and resiliently reposition teeth from one arrangement to a successive arrangement. This is possible because the cavities are shaped to fit a mold of digitally arranged teeth in the successive arrangement. A full description of an exemplary elastic repositioning appliance shaped in this manner is described in U.S. Pat. No. 5,975,893, and in published PCT application WO 98/58596. Placement of the elastic positioner over the teeth applies controlled forces in specific locations to gradually move the teeth into the new configuration. In order to apply sufficient force, the appliance generally covers the tooth surfaces and portions of the gingival margin. Thus, both individual repositioning appliances and systems of such elastic repositioning devices may be used to deliver agents to the underlying tooth surfaces and gingiva comprising the oral environment while repositioning teeth.

In a first embodiment, the oral delivery appliance delivers fluoride to the oral environment to prevent or treat tooth decay. Traditionally, fluoride has been delivered to the oral environment through the use of toothpastes, gels, rinses and varnishes, to name a few. The present invention provides fluoride delivery which may be used in conjunction with traditional applications or may replace certain applications. Such fluoride may be provided in a number of forms, such as neutral sodium fluoride, stannous fluoride, hydrogen fluoride, or acidulated phosphate fluoride (APF) gel, for example. Fluoride may be releasably attached to the elastic repositioning appliance in a number of forms, as will be described in more detail in later sections, to provide delivery to the oral environment.

In a second embodiment, the oral delivery appliance delivers an antibiotic or drug to the oral environment. In the case of antibiotics, delivery of such an agent may inhibit or kill various microorganisms. Antibiotics often used to treat gingivitis and periodontitis include chlorhexidine and tetracycline. Such antibiotics may be releasably attached to the elastic repositioning appliance in a number of forms, as will be described in more detail in later sections, to provide delivery to the oral environment.

In a third embodiment, the oral delivery appliance delivers a bleaching material to the oral environment. Bleaching of the teeth is a common cosmetic procedure requested of dental practitioners by their patients. The active ingredient in standard bleaching gels is carbamide peroxide and is typically present in an 18-37% suspension. Bleaching materials, such as carbamide peroxide, may be releasably attached to the elastic repositioning appliance in a number of forms, as will be described in more detail in later sections, to provide delivery to the oral environment.

In a fourth embodiment, the oral delivery appliance delivers a breath freshener to the oral environment. Breath fresheners are commonly available in a number of flavors and scents, including mint and fruit flavors, derived from essential oils and/or natural or artificial flavorings, to name a few. Such breath fresheners may be releasably attached to the elastic repositioning appliance in a number of forms, as will be described in more detail in later sections, to provide delivery to the oral environment.

In a second aspect of the present invention, at least some of the elastic repositioning appliances in a system for repositioning teeth are coupled to means for releasing the agent to the oral environment when the appliance is placed over the teeth. Such means may comprise a layer which includes the agent. The layer may be formed over at least a portion of the surfaces of the repositioning appliance. These surfaces include both the cavity surfaces, the surfaces within the cavities which contact the teeth when in place, and the external surfaces, the surfaces of the appliance which contact the cheeks and lips when in place. The layer may be comprised of various materials and may take a variety of forms. For example, the layer may consist essentially of the agent. In other words, the agent may be attached directly to a surface of the polymer shell of an elastic repositioning appliance. This may be achieved by applying the agent (optionally in an inert carrier or diluent) itself to the surface utilizing a number of methods, such as spraying, painting and/or dipping. When the repositioning appliance is placed over the patient's teeth, the agent may then be released to the oral environment.

Alternatively, the layer may comprise the agent present in or on a carrier or binder which promotes adhesion or attachment to the appliance and/or which creates a matrix from which the agent can be released by diffusion or dissolution. In one embodiment, the agent is dissolved in the carrier or binder. In this case, the agent may be provided in powder or similar form and dissolved in a liquid solvent. The result may be a solution which may be applied to a surface of the shell, typically by spraying, painting and/or dipping, to form a coating or film. When the repositioning appliance is placed over the patient's teeth, the agent may then be released from the coating to the oral environment. Release may be due to activation or deactivation of the carrier or any other releasing mechanism, such as by enzymes or proteins in saliva. Or release may be due to degradation of the carrier by contact with, for example, saliva. In some cases, the binder or carrier may evaporate upon application to the layer to the surface leaving the agent behind. In these cases, the agent may be released in a similar fashion as when the agent is directly attached to the surface, as described above. It may be appreciated that any agent, particularly fluoride materials, antibiotics, bleaching materials and breath fresheners, may be delivered to the oral environment in this manner.

In another embodiment, the agent is encapsulated or suspended in the layer. A common material for suspension of an agent is a semisolid material, such as a gel, jelly or putty. Such a material may be applied to a surface of the shell by spraying, painting and/or dipping to form a coating or film. Here, as in all cases, suspension is not limited to a scientific definition and may refer to any situation in which a carrier holds, contains, supports or otherwise includes an agent. Alternatively or in addition, the semisolid material may be deposited in the cavities of the polymer shell which are shaped to receive the teeth. The cavities may be filled to any desired level. When the repositioning appliance is positioned over the teeth, the teeth will directly contact the semisolid material in the cavities and displace any extra material as the teeth are inserted into the cavities. Therefore, it is desired to fill the cavities to a level which will avoid excess overflow of the material from the appliance. Delivery of an agent by use of a semisolid suspension material is common in bleaching treatments and fluoride treatments, for example. However, such treatments apply the material with the use of a tray or generic appliance which does not apply repositioning forces to the teeth. By modifying a repositioning appliance, as described above, orthodontic treatment may continue throughout the delivery of such agents. It may be appreciated that any agent, particularly fluoride materials, antibiotics, bleaching materials and breath fresheners, may be delivered to the oral environment in this manner.

Another common material for encapsulation or suspension of an agent is a controlled-release material. Thus, the layer may be comprised of a rate-controlling material wherein the rate controlling material controls the rate at which the agent is released from the layer. Controlled-release or rate-controlled materials deliver a predetermined amount of an agent at a predetermined rate. Often such delivery maintains a steady-state concentration of an agent in an environment within a desired therapeutic range for a prolonged period of time. Thus, a prescribed dosage may be delivered. In addition, the ability to sustain delivery eliminates the need for repeated applications of the agent for dosed delivery to the oral environment.

Although such controlled release materials may be provided as a semisolid material, such as a gel, jelly or putty, as described above, these materials may also be provided as a solid material which is attached to the polymeric shell of the repositioning appliance. One type of controlled-release material comprises a polymer matrix membrane within which finely dispersed particles of an agent are suspended. The agent may diffuse through the matrix membrane according to a concentration gradient. Alternatively or in addition, the agent may be released by degradation of the polymer matrix membrane material. In either case, the controlled-release material may be provided as a sheet which may be laminated to a surface of the shell. The controlled-release sheet may be layered with the elastomeric polymer and vacuum formed over a mold to form the repositioning appliance. The controlled-release material may be arranged so that it is present on the inside or outside surfaces of the appliance depending on the material and desired application. Or, the controlled-release sheet may be laminated or bonded to a surface of the polymeric shell after forming to supply agent delivery in desired areas. Alternatively, the controlled-release material may be provided as a tablet or similar mass which may be inserted into the polymeric shell of the repositioning appliance. The agent may then elute from the tablet into the oral environment over time.

In another embodiment, the agent may be held within pores of a material and may elute out at a controlled rate from the pores. The agent itself may be absorbed into the pores of the material, or the agent may be suspended in a carrier which is absorbed into the pores of the material. In the latter case, the agent may be released from the carrier by diffusion and/or by controlled degradation of the carrier material. This may incorporate a rate-controlling mechanism in addition to the controlled-release of the agent from the pores. As mentioned, in some cases, enzymes in the patient's saliva will activate the release or degrade the carrier material to release the agent. It may be appreciated that the agent may be released by a combination of any of the release methods.

In a further embodiment, the polymeric shell of the repositioning appliance itself comprises a controlled-release material containing the agent. In this case, at least a portion of at least some of the polymeric shells in a system for repositioning teeth are formed from a controlled release material wherein the rate controlling material controls the rate at which the agent is released from the shell. As previously described, the controlled-release material may be a provided in the form of a sheet. Thus, the sheet of controlled-release material may be vacuum formed over a mold of the patient's teeth to form a repositioning appliance itself. In this manner, no additional elastomeric materials may be needed to form the appliance. The controlled-release material may be a polymer matrix membrane, a porous material or any suitable material. Controlled-release may be designed so that the elution rate of the agent corresponds to the repositioning rate of the teeth. The agent may elute throughout the repositioning process, concluding as the teeth reach the desired arrangement prescribed by the appliance.

In a still further embodiment, the releasing means coupled to at least some of the repositioning appliances comprises a reservoir formed in the shell of the appliance in addition to the cavity which receives the teeth. Typically, a rate controlling membrane is disposed over the reservoir wherein the rate controlling membrane controls the rate at which the substance is released from the reservoir. The reservoir may be pre-filled or pre-loaded with an agent or substance for delivery. In this case, the appliance may be ready for insertion or use upon removal from any packaging without the need of loading the appliance with the agent for delivery. If the releasing means is designed for a single delivery period, the appliance may be worn throughout the prescribed repositioning period and then disposed of. If the releasing means is designed for multiple delivery periods, the reservoir may be replenished with the agent to be released any number of times throughout the prescribed repositioning period. It may be appreciated that any agent, particularly fluoride materials, antibiotics, bleaching materials and breath fresheners, may be delivered to the oral environment in this manner.

In some instances, it may be desirable to change a visual characteristic of the polymeric shell of an oral appliance. Such appliances comprise a polymeric shell having a cavity shaped to be removably placeable over the teeth and a material on or within the shell that changes a visual characteristic of the shell. Such a change is typically in response to a change in the environment. In some cases, the visual characteristic is a color, such as green, red or blue. Thus, the appliance may appear colored or a particular color under certain environmental conditions, either in the oral environment or when removed. The described material may be a dye which changes color in response to a change in temperature. For example, the dye may change color when the appliance is removed from the mouth and changes temperature from body temperature (37.degree. C.) to room temperature (25.degree. C.). Similarly, the dye may change color when the appliance is rinsed with cool water.

Other objects and advantages of the present invention will become apparent from the detailed description to follow, together with the accompanying drawings.

DESCRIPTION

FIG. 1 shows an exemplary removable appliance 15 adapted to fit over teeth on a jaw 16. A usage indicator 100 can be mounted on one tooth or on the appliance 15 to indicate patient compliance.

In one implementation, the indicator 100 can be a coat on a tooth or an appliance with a chemical agent. Alternatively, the indicator 100 can be an electrical agent, optical agent or mechanical agent that indicates appliance wearage. In one embodiment, the indicator agent is inactive until contact with liquid or moisture. Alternatively, release of the agent can be stimulated by liquid or moisture. Thus, in one case, upon wearing, oral fluids activates the agent and allows the agent to seep out and indicate compliance. Alternatively, oral fluids such as saliva, among others, can seep in to activate the agent to indicate compliance.

In another embodiment, the appliance can release a coloring agent to the oral environment when the appliance is worn over the teeth. Such means may comprise a layer which includes the agent. The layer may be formed over at least a portion of the surfaces of the repositioning appliance. These surfaces include both the cavity surfaces, the surfaces within the cavities which contact the teeth when in place, and the external surfaces, the surfaces of the appliance which contact the cheeks and lips when in place. The layer may be comprised of various materials and may take a variety of forms. For example, the layer may consist essentially of the agent. In other words, the agent may be attached directly to a surface of the polymer shell of an elastic repositioning appliance. This may be achieved by applying the agent (optionally in an inert carrier or diluent) itself to the surface utilizing a number of methods, such as spraying, painting and/or dipping. When the repositioning appliance is placed over the patient's teeth, the agent may then be released to the oral environment.

Alternatively, the layer may comprise the agent present in or on a carrier or binder which promotes adhesion or attachment to the appliance and/or which creates a matrix from which the agent can be released by diffusion or dissolution. In one embodiment, the agent is dissolved in the carrier or binder. In this case, the agent may be provided in powder or similar form and dissolved in a liquid solvent. The result may be a solution which may be applied to a surface of the shell, typically by spraying, painting and/or dipping, to form a coating or film. When the repositioning appliance is placed over the patient's teeth, the compliance indicating agent may then be released from the coating to the oral environment. Release may be due to activation or deactivation of the carrier or any other releasing mechanism, such as by enzymes or proteins in oral fluids. Or release may be due to degradation of the carrier by contact with, for example, oral fluids. In some cases, the binder or carrier may evaporate upon application to the layer to the surface leaving the agent behind. In these cases, the agent may be released in a similar fashion as when the agent is directly attached to the surface, as described above. It may be appreciated that any agent, particularly fluoride materials, antibiotics, bleaching materials and breath fresheners, may be delivered to the oral environment in this manner.

In another embodiment, the agent is encapsulated or suspended in the layer. A common material for suspension of an agent is a semisolid material, such as a gel, jelly or putty. Such a material may be applied to a surface of the shell by spraying, painting and/or dipping to form a coating or film. Here, as in all cases, suspension is not limited to a scientific definition and may refer to any situation in which a carrier holds, contains, supports or otherwise includes an agent. Alternatively or in addition, the semisolid material may be deposited in the cavities of the polymer shell which are shaped to receive the teeth. The cavities may be filled to any desired level. When the repositioning appliance is positioned over the teeth, the teeth will directly contact the semisolid material in the cavities and displace any extra material as the teeth are inserted into the cavities. Therefore, it is desired to fill the cavities to a level which will avoid excess overflow of the material from the appliance. Delivery of an agent by use of a semisolid suspension material is common in bleaching treatments and fluoride treatments, for example. However, such treatments apply the material with the use of a tray or generic appliance which does not apply repositioning forces to the teeth. By modifying a repositioning appliance, as described above, orthodontic treatment may continue throughout the delivery of such agents. It may be appreciated that any agent, particularly fluoride materials, antibiotics, bleaching materials and breath fresheners, may be delivered to the oral environment in this manner.

Another common material for encapsulation or suspension of an agent is a controlled-release material. Thus, the layer may be comprised of a rate-controlling material wherein the rate controlling material controls the rate at which the agent is released from the layer. Controlled-release or rate-controlled materials deliver a predetermined amount of an agent at a predetermined rate. Often such delivery maintains a steady-state concentration of an agent in an environment within a desired therapeutic range for a prolonged period of time. Thus, a prescribed dosage may be delivered. In addition, the ability to sustain delivery eliminates the need for repeated applications of the agent for dosed delivery to the oral environment.

Although such controlled release materials may be provided as a semisolid material, such as a gel, jelly or putty, as described above, these materials may also be provided as a solid material which is attached to the polymeric shell of the repositioning appliance. One type of controlled-release material comprises a polymer matrix membrane within which finely dispersed particles of an agent are suspended. The agent may diffuse through the matrix membrane according to a concentration gradient. Alternatively or in addition, the agent may be released by degradation of the polymer matrix membrane material. In either case, the controlled-release material may be provided as a sheet which may be laminated to a surface of the shell. The controlled-release sheet may be layered with the elastomeric polymer and vacuum formed over a mold to form the repositioning appliance. The controlled-release material may be arranged so that it is present on the inside or outside surfaces of the appliance depending on the material and desired application. Or, the controlled-release sheet may be laminated or bonded to a surface of the polymeric shell after forming to supply agent delivery in desired areas. Alternatively, the controlled-release material may be provided as a tablet or similar mass which may be inserted into the polymeric shell of the repositioning appliance. The agent may then elute from the tablet into the oral environment over time.

In another embodiment, the agent may be held within pores of a material and may elute out at a controlled rate from the pores. The agent itself may be absorbed into the pores of the material, or the agent may be suspended in a carrier which is absorbed into the pores of the material. In the latter case, the agent may be released from the carrier by diffusion and/or by controlled degradation of the carrier material. This may incorporate a rate-controlling mechanism in addition to the controlled-release of the agent from the pores. As mentioned, in some cases, enzymes in the patient's oral fluids will activate the release or degrade the carrier material to release the agent. It may be appreciated that the agent may be released by a combination of any of the release methods.

In a further embodiment, the polymeric shell of the repositioning appliance itself comprises a controlled-release material containing the agent. In this case, at least a portion of a polymeric shell is formed from a controlled release material wherein the rate controlling material controls the rate at which the agent is released from the shell. As previously described, the controlled-release material may be a provided in the form of a sheet. Thus, the sheet of controlled-release material may be vacuum formed over a mold of the patient's teeth to form a repositioning appliance itself. In this manner, no additional elastomeric materials may be needed to form the appliance. The controlled-release material may be a polymer matrix membrane, a porous material or any suitable material. Controlled-release may be designed so that the elution rate of the agent corresponds to the repositioning rate of the teeth. The agent may elute throughout the repositioning process, concluding as the teeth reach the desired arrangement prescribed by the appliance.

In a still further embodiment, the releasing means coupled to at least some of the repositioning appliances comprises a reservoir formed in the shell of the appliance in addition to the cavity which receives the teeth. Typically, a rate controlling membrane is disposed over the reservoir wherein the rate controlling membrane controls the rate at which the substance is released from the reservoir. The reservoir may be pre-filled or pre-loaded with an agent or substance for delivery. In this case, the appliance may be ready for insertion or use upon removal from any packaging without the need of loading the appliance with the agent for delivery. If the releasing means is designed for a single delivery period, the appliance may be worn throughout the prescribed repositioning period and then disposed of. If the releasing means is designed for multiple delivery periods, the reservoir may be replenished with the agent to be released any number of times throughout the prescribed repositioning period. It may be appreciated that any agent, particularly fluoride materials, antibiotics, bleaching materials and breath fresheners, may be delivered to the oral environment in this manner.

In some instances, it may be desirable to change a visual characteristic of the polymeric shell of an oral appliance. Such appliances comprise a polymeric shell having a cavity shaped to be removably placeable over the teeth and a material on or within the shell that changes a visual characteristic of the shell. Such a change is typically in response to a change in the environment. In some cases, the visual characteristic is a color, such as green, red or blue. Thus, the appliance may appear colored or a particular color under certain environmental conditions, either in the oral environment or when removed. The described material may be a dye which changes color in response to a change in temperature. For example, the dye may change color when the appliance is removed from the mouth and changes temperature from body temperature (37° C.) to room temperature (25° C.). Similarly, the dye may change color when the appliance is rinsed with cool water.

The appliance can be used to provide an intra-oral drug delivery system. In addition to the agents described above, other compounds can be used as well. For example, a drug coated appliance can be used to deliver desensitizing medication to sensitive teeth. The drug substance can simply be a small amount of the active ingredient in a desensitizing toothpaste or gel, such as Sensodyne®. The desensitizing agent is dispersed throughout the surface of the appliance and is delivered, at a substantially constant rate, to the patient's sensitive teeth for a relatively extended period of time.

Although the appliance may be pre-loaded with the agent and ready for use upon removal from any packaging, appliances that are not pre-filled or pre-loaded may require loading prior or immediately prior to placing the appliance over the teeth. Loading may comprise placing the agent in a teeth-receiving cavity. As described previously, the cavities may be filled to any desired level. When the appliance is positioned over the teeth, the teeth will directly contact the agent in the cavities as the teeth are inserted into the cavities. Alternatively, loading may comprise placing the agent into an agent release reservoir in the appliance immediately prior to placing the appliance over the teeth. The agent will then elute from the reservoir into the oral environment when the appliance is in place over the teeth. The elution rate may be controlled by a controlled release membrane which separates the reservoir from the surrounding environment. Loading may also comprise adhering a rate controlling material containing the agent to a surface of the appliance prior to placing the appliance over the teeth. Such a material may comprise a polymer matrix membrane which may be removably or permanently adhered to the polymeric shell of the appliance in desired areas for delivery of the agent. And finally, loading may comprise absorbing the agent into a porous material on or within the appliance immediately prior to placing the appliance over the teeth.

Means for releasing the agent may include a number of embodiments, including any such means previously described. Typically, means for releasing the agent comprises a layer including the agent, as previously described, and coupling comprises adhering the layer to at least a portion of a surface of the appliance. When the layer consists essentially of the agent, adhering may involve coating, spraying, dipping or painting the agent on the surface of the appliance. Thus, a pre-formed appliance may simply be coated with the agent prior to insertion in the patients mouth. When the layer comprises an agent present in or on a carrier or binder, adhering may involve attaching the carrier or binder a surface of the appliance. Similarly, when the agent is encapsulated in the layer, the layer may be attached to the surface of the appliance. The layer may comprise a sheet of rate controlling material wherein the rate controlling material controls the rate at which the agent is released from the layer. In this case, the sheet may be bonded to the surface of the appliance with an adhesive. Alternatively, the sheet may be attached to the surface by press fitting. The sheet and the surface may each be shaped so that they snap or fit together by pressing them together. For example, the sheet may have a formed protrusion and the surface a formed inset, wherein the protrusion fits into the inset when pressed upon the inset and holds the sheet in place. In many instances, the appliance may be porous or have a reservoir which can be loaded with a desired agent at any time the treating professional and/or the patient decide that it is appropriate. For example, an appliance can be immersed in a solution of the agent, allowing the appliance to absorb or adsorb the agent at a particular time.

In addition, the sheet may be preformed to a shape adapted for fitting against the surface of the appliance or a surface of the teeth or gingiva. For example, the sheet may be pre-formed to reflect the shape of the surface of one or more teeth or the gingiva, particularly along the gingival margin. The preformed sheet may then be held against that surface when the sheet is coupled to the appliance and the appliance is placed over the teeth. Coupling may involve any means of attaching the sheet to the appliance. In particular, the pre-formed sheet may further comprise an adhesive layer which may provide bonding of the sheet to the surface of the appliance.

The material to make to the appliance of FIG. 1 can be supplemented with additional fillers such as electrically conducting fillers, magnetic fillers, illuminating fillers, piezo-electric fillers, and/or light sensitive fillers. The material properties of the appliance made with or without these additional fillers such as modulus, electrical resistance, material permeability, and birefringence (degree of orientation of the material or stress), illuminating patterns or patterns under special light sources may change after the appliance is worn over time, as these properties are altered due to changes in structure, organization, and/or spatial spacing between the fillers. For example, it is well established that electrical conductivity of filled composites scales with filler volume concentration according to percolation theory. Therefore, mechanical deformation or thermal expansion of the non-conductive polymer matrix will lead to increased average inter-filler spacing, or decreased filler volume concentration, and consequently decreased electrical conductivity. Examples of electrically conductive fillers include metals, graphite, electrically conductive polymers, semiconductors, and superconductors. These changes in properties can be used as an indicator for compliance and can be diagnosed by instrumentation. Similarly, separation of conductive fillers will also lower thermal conductivity, which can also be measured by instrumentations. If the fillers have magnetic behavior in the presence of external stimulation, such as diamagnetics (Cu, Au, Ag, etc.) and paramagnetics (e.g. Al, Cr, Na, Ti, Zr, etc.); or exhibit intrinsic magnetic properties, such as ferromagnetics (Fe, Co, Ni, etc.), antiferromagnetics (e.g. MnO), and ferromagnetics (MFe2O4), then separation of the filler spacing due to mechanical deformation of the polymer matrix can also lead to decreases in magnetic properties above the Curie temperature. Mechanical deformation of composites with illuminating fillers, such as those that exhibit luminescence, fluorescence, or phosphorescence, will result in decreased illumination intensity. Bending deformation or displacement of piezoelectric fibers can result in electrical potentials which can be either measured, or used to activate other electrically driven indicators (e.g. low power LED light). Fillers with optical properties which depend on external electric field, for example those that shift their absorption coefficients in the UV, IR, or visible spectrum can also serve as indicator of matrix deformation.

Figure 2A:
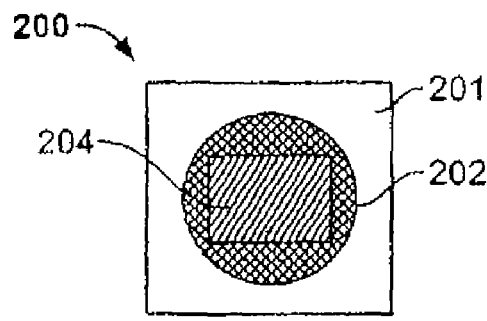
FIGS. 2A-2C show a first embodiment of the compliance indicator of FIG. 1.

Referring now to FIG. 2A, an embodiment of an indication attachment device 200 is shown. The indication attachment device 200 includes a polymer well 201, and the well 201 includes a semi-permeable membrane 202. The membrane 202 allows a two-way flow between the well 201 and an interface to the oral environment. Within the well 201, a material 204 such as a dyed material is provided.

In one embodiment, the dyed material 204 is a releasable material, such as dyed poly(vinylsiloxane) (PVS) material. The PVS material is used to hold the dye, and the membrane 202 can be a cellulose acetate membrane. Those skilled in the arts will understand that other releasable materials such as polyether, polyurethane, ethyl vinyl acetate can also be manipulated to result in the teachings of this patent.

In another embodiment, the material 204 can be an enzyme or a reactor that reacts with enzymes from the oral fluids. When oral fluids or enzyme from the oral fluids enters the well, the material 204 reacts with the enzyme to provide an indication. Alternatively, a pH indicator can be used as the material 204. In yet another embodiment, the membrane 202 can be silicon instead of PVS.

In another embodiment, the polymer can be water-soluble polymer that includes water-soluble polymers, lightly cross-linked hydrogels, and high molecular weight with hydrogen bonding plastics that demonstrate some limited water resistance. Natural-based water-soluble polymers include starch, starch-oxided, cellulose, cellulose-alkoxylated, cellulose-carboxyalkylated, chitin, chitosan, pectins, hyaluronic acid, proteins, and lignin. Water-soluble polymers can also be created from synthetic raw material through polymerization by addition/vinyl, condensation, and ring-opening. Examples of these types of polymers are poly(vinyl alcohol), polyesters, and poly(alkylene oxides). The hydrolytic instability of biodegradable polymers is advantageous because the presence of the oral fluids will facilitate the degradation of the polymer.

Figure 2B:
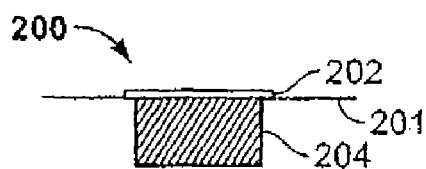
Figure 2C:
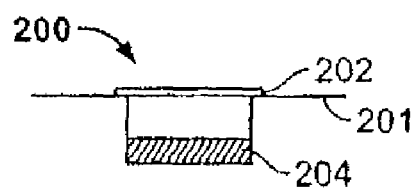

Referring now to FIG. 2B, a cross-sectional view of the compliance indication attachment device (compliance indicator) 200 is shown. As viewed therein, the membrane 202 is positioned above the polymer well, chamber or housing 201 with the releasable material and or dye 204 enclosed therein. As shown in FIG. 2C, after a predetermined period of time, for example two weeks, a portion of the dyed PVS material 204 has seeped out causing a change in appearance of the indication attachment device. The dye is released while the PVS stays inside the device. In this case, a color change can occur or alternatively, the volume of the material has changed, in this case it has reduced in size.

In one embodiment, the compliance indicator 200 has a clear, tooth-colored, or esthetically pleasing polymer reservoir well, chamber or housing 201. A transparent or translucent semi-permeable membrane 202 separates the content within the reservoir chamber 201 from the external oral environment. The content(s) within the reservoir chamber 201 depends on the overall strategy to monitor compliance. In one implementation, contents diffuse out from the reservoir chamber 201, through the membrane 202, into the external environment. For example: the content can be an FDA approved visible dye which diffuses from the chamber 201, through the membrane 202, and into the external oral environment. When the content is emptied, the content color diminishes in brightness and value. Colorants that are permitted for direct addition to human food by the US FDA include annatto extract, beta-carotene, beet powder, canthaxanthin, caramel color, carrot oil, cochineal extract (carmine); cottonseed flour, fruit juice, paprika, riboflavin, saffron, turmeric, vegetable juice, FD&C Blue No. 1 (brilliant blue) and No. 2 (indigotine), FD&C Green No. 3 (fast green FCF), FD&C Red No. 3 (erythrosine) and No. 40 (allura red), FD&C Yellow No. 5 (tartrazine) and No. 6 (sunset yellow). Other food colorants such as those found at FDA's Center for Food Safety and Applied Nutrition website: http://www.cfsan-.fda.gov/-dms/col-toc.html can be used as well.

In another implementation, matter from the external environment diffuse in, and reacts with the contents 204 within the reservoir chamber 201. For example, glucose molecules from the external environment diffuse through the membrane 202, and reacts with enzymes inside the content and the resultant enzymatic products interact with other reactants inside the content to cause color change. As more glucose molecules diffuse in, content color increases in brightness and value. A convenient enzyme system is glucose oxidase and horseradish peroxidase. The first enzyme, glucose oxidase, catalyzes the oxidation of glucose to form gluconic acid and hydrogen peroxide. Hydrogen peroxide then reacts with 3-3,5,5'-tetramethylbenzidine (TMB) under catalytic action of horseradish peroxidase to convert yellow TMB to green. Other colorants, such as potassium iodide (green to brown) may also be used. These enzymes can be immobilized within the chamber. The rate of reaction, and hence color change, can be controlled by selecting the permeability of the membrane 202, the concentration of reactants inside the chamber 201, and the method of delivery. The rate of reaction or concentration of the glucose molecules can also be detected through spectroscopy or other analytical testing. Test results will correlate with compliance to treatment.

Figure 3A:
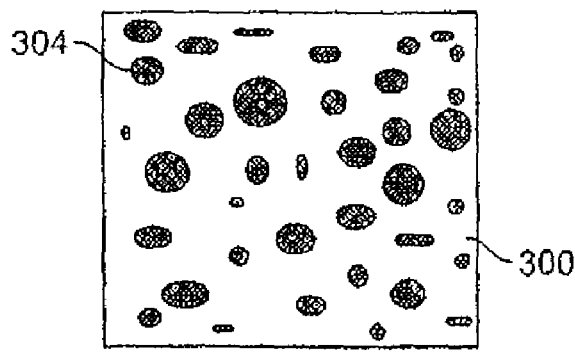
FIGS. 3A-3B show a second embodiment of the compliance indicator of FIG. 1.
Figure 3B:
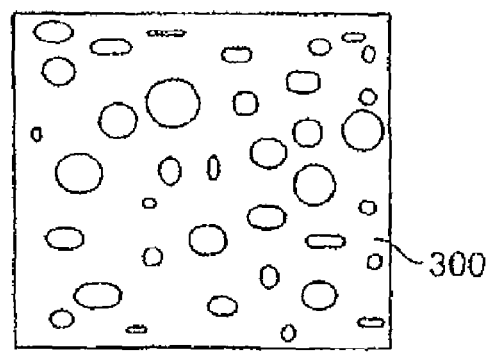

Referring now to FIGS. 3A and 3B, another embodiment of an indication attachment device is shown. In the embodiment of FIG. 3A, a porous polymer material is provided on a sheet 300. The polymer material is disposed on the sheet 300 as one or more containers 304. The container 304 may be a well as disclosed above in the discussion of FIGS. 2A-2C. After a predetermined period of usage, the polymer material changes appearance, for instance, changes either to the color or the size as shown in FIGS. 2B-2C. Other implementations can include colored polymers (both thermoplastic and thermoset materials) and composites utilizing the same compliance mechanism as the porous polymer material.

The compliance indicator of FIGS. 3A-3B thus can be a dye encapsulated in a polymer which is released in the presence of oral fluids. The dye can be colorants that react with the oral fluids and that are released from the polymer. The polymer can be porous polymer such as monolithic porous polymer (currently used in chromatography), PVS, a high internal phase emulsion (HIPE polymer currently used in drug release) or any macroporous polymer. The dyed polymer will be constructed into a small button that can be bonded to the exterior of the aligner. The amount of dye loss will correspond with the amount of time the aligner was in use. The pore size of the polymer and the particle size of the dye will affect the rate of diffusion of dye from the button to the oral fluids environment and depending on compliance needs, these factors can be controlled.

Porous polymers are prepared by adding "porogens" during the polymerization process of resins. Porogens are soluble in the monomer but insoluble in formed polymers. As polymerization occurs, pores are formed in the spaces where porogens are found. The newest type of porous polymers is known as "high internal phase emulsions" ("HIPE"). HIPE structures have pore diameters much larger than previous porous materials which had only pore diameters in the angstroms.

Another porous polymer is the monolithic porous polymer currently being used in chromatography. The polymerization of this rigid macroporous polymer takes the shape of the mold, usually a column, into which the monomers and porogens are poured into. Generally, the pore volume is nearly equal to the amount of porogens added into the monoliths.

Figure 4A:
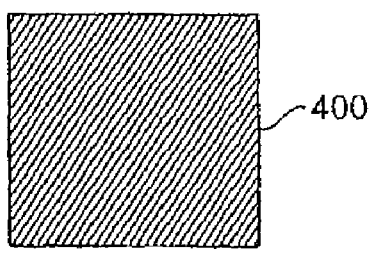
FIGS. 4A-4B show a third embodiment of the compliance indicator.
Figure 4B:

Referring now to FIGS. 4A and 4B, a button embodiment of an indication attachment device 400 is shown. In this embodiment, a biodegradable polymer material is attached to either a tooth or a dental appliance. After a certain period of use, the polymer material either changes shape or size or color, and as shown in FIG. 4B, the volume of the biodegradable polymer material is subsequently reduced. In one embodiment, the button is a biodegradable polymer button. The button can be molded from a biodegradable polymer and bonded to the exterior of the aligner. The button will have a predetermined degradation period such as a two week degradation period in the constant presence of oral fluids. Potentially the polymer can be colored for a more visible indication of the degradation of the button. The size and material will determine the degradation period of the button. However, other factors such as brushing of the aligner and rinsing will have to be taken into consideration when determining the optimal degradation time of the button.

The degradation products often define the biocompatibility of a polymer. Synthetic biodegradable polymers are favored over natural ones because of reliability of raw materials. The following is a list of common biodegradable polymers: polyglycolide (PGA), polylactide (PLA), 1-lactide (LPLA), poly (dl-lactide) (DLPLA), poly(E-caprolactone) (PCL), polydioxanone (PDO), poly(glycolide-co-trimethylene carbonate) (PGA-TMC), and polyorthoesters.

Figure 5:
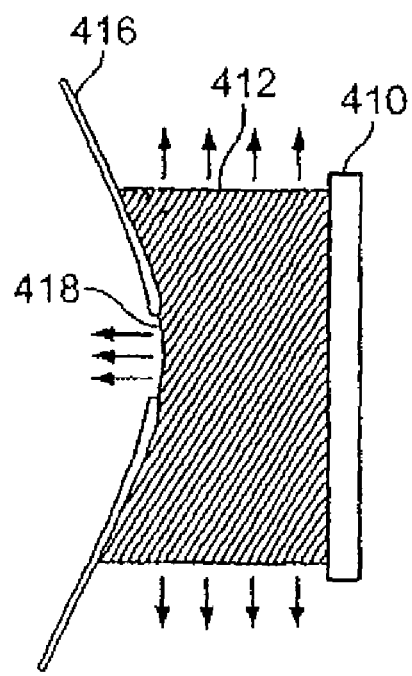
FIG. 5 shows a fourth embodiment of the compliance indicator.

FIG. 5 shows yet another embodiment of an indication attachment device. In this embodiment, an appliance 416 receives an adhesive dye matrix 412. The matrix 412 is sealed either at one end or both ends using a backing film 410. The material in the matrix 412 can be released on the sides between the appliance 416 and the film 410 or between the two backing films. An opening 418 may be provided in the appliance 416 and one side of the backing film to facilitate dye release. In one implementation, a transdermal patch may be applied in a manner similar to drug releasing transdermal patches. Instead of embedding and releasing drug in the adhesive matrix, a dye is released and the mechanism for dye loss is moisture (oral fluids). In one implementation, appliance wear compliance is indicated by the color of the adhesive layer: the more dye lost, the longer the wear time.

Figure 6:
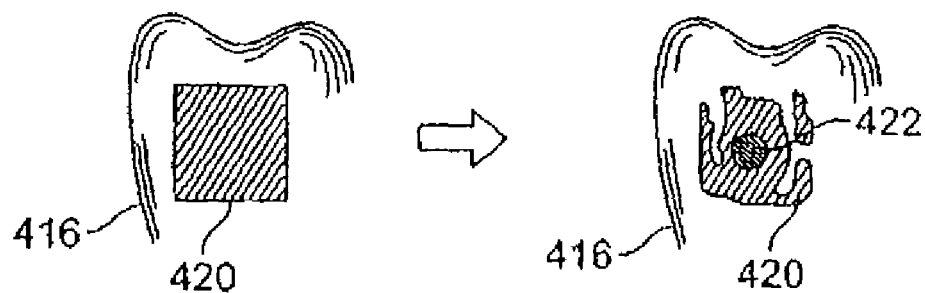
FIG. 6 shows a fifth embodiment of the compliance indicator.

FIG. 6 shows yet another embodiment where the wear indication is achieved through a water dissolvable film. In this embodiment, an opaque water soluble film 420 is positioned to cover one or more colored areas, regions, spots, or dots 422 on an appliance or on a tooth. The dots 422 can be a series of colored dots with varying thicknesses of film 420 and each exposed color corresponds to a different amount of appliance wear time. In the embodiment where the dots 422 are imprinted on the appliance, the film 420 is layered onto the surface of the appliance. The mechanism of releasing dye is moisture (oral fluids).

Figure 7:
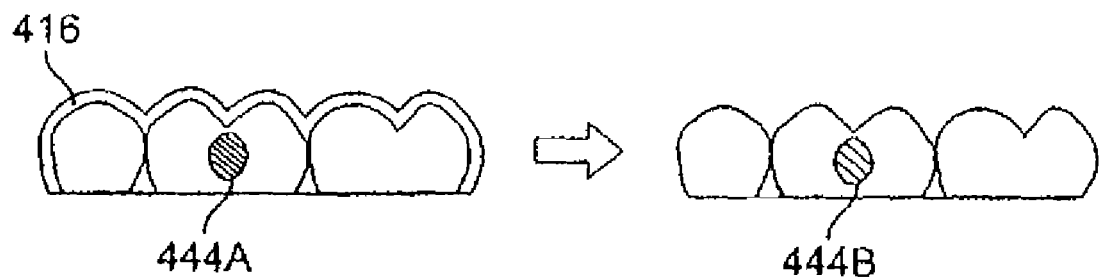
FIG. 7 shows a sixth embodiment of the compliance indicator.

FIG. 7 shows another embodiment where a tooth attachment 444A is made with a dye-releasing composite. The dye-releasing composite 444A bonded to a tooth will be covered by an appliance 416. Over time, the dye-releasing composite 444A has a reduced or no color loss compared to the loss for a dye on an uncovered tooth attachment 444B. The color of the attachment will correspond to the amount of aligner wear. The mechanism of dye releasing is moisture (oral fluids) in this embodiment.

In yet other implementations, a diagnostic indicator can be provided. The diagnostic indicator is similar in device construction to the compliance indicator, and utilizes the inwards diffusion strategy, where biochemical analytes from the external environment are allowed to diffuse through the membrane to react with the contents within the reservoir chamber. Thus, biomarkers from the external environment diffuse through the membrane, and react with reagents inside the content to directly or indirectly induce color change or chemical change that can be quantified through human eye or laboratory testing or computerized vision systems. As more biomarkers diffuse into the diagnostic indicator, the content color changes, for example increases in brightness and value. Possible biomarkers include enzymes, pH, glucose, salt, oral film, plaque, microorganisms that may exist in the oral cavity and amount of oral fluids.

Figure 8:
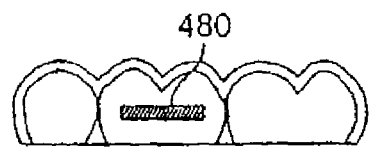
FIG. 8 shows a seventh embodiment of the compliance indicator.

In one embodiment shown in FIG. 8, the compliance indicator can be a time temperature indicator 480. The indicator 480 is intra-orally placed in the mouth (either directly on a tooth or on an appliance 470) and provides an indication of the time the indicator has been at a preselected intra-oral temperature environment.

Figure 9:
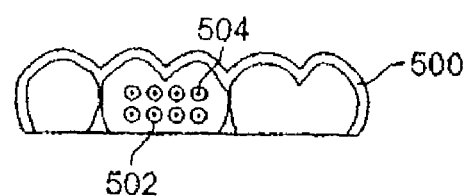
FIG. 9 shows an eighth embodiment of the compliance indicator.

In yet another embodiment shown in FIG. 9, a plurality of brushes 502 having a colored fiber 504 is positioned on the appliance 500. As the brush 502 is gradually eroded by wearing the appliance 500, a dye or other suitable indicia of wear in the fiber 504 is exposed for visual detection by a human or by a machine. Alternatively, the brushes 502 can be placed on one or more teeth instead of on the appliance 500.

In yet another embodiment, the compliance indication is human readable by changing physical or mechanical or visual properties that are readily observable by a human. In other embodiment, the compliance indication is machine readable. For instance, in one embodiment that alters the electrical characteristics of an appliance during wearing of the appliance, an electrical measurement can be made by a computer for detecting compliance. In another embodiment that uses biomarkers, a computer with biomarker sensor can be used with suitable computer program to detect compliance. In yet another embodiment, a color change can be detected by a computer vision program to detect compliance.

Each computer program is tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

Dental and periodontal therapies may be simultaneously delivered by an elastic repositioning appliance to provide uninterrupted orthodontic treatment while treating other conditions. Such therapies include fluoride treatment to prevent or treat tooth decay, antibiotic or drug therapy to treat gingivitis and periodontitis, bleaching to improve the cosmetic appearance of the teeth, and/or breath freshening to treat halitosis. In addition, such an elastic repositioning appliance may also comprise a material which changes a visual characteristic of the shell in response to a change in the environment, as stated previously.

Each of the above identified therapies involves one or more therapeutic agents which are delivered to the oral environment. The present invention provides a tooth positioning appliance coupled to means for releasing one or more of these agents to the oral environment. Agents for the above identified therapies include, but are not limited to, various forms of fluoride, such as neutral sodium fluoride and stannous fluoride, various antibiotics, such as chlorhexidine and tetracycline, bleaching ingredients, such as carbamide peroxide, and breath fresheners or flavors. Means for releasing the agent may include a number of embodiments.

Figure 10:
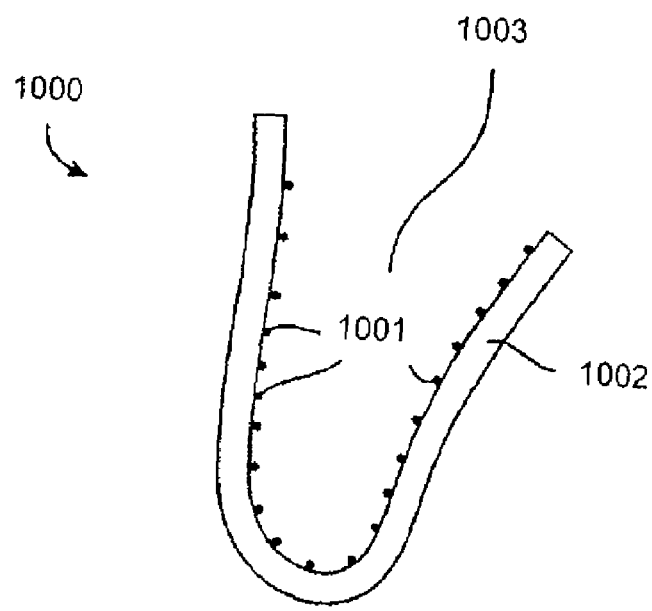
FIG. 10 is a cross-sectional view of the repositioning appliance with a layer comprising an agent on its surface.

In one embodiment, means for releasing the agent to the oral environment comprises a layer including the agent formed over at least a portion of the surfaces of the polymer shell. Such a layer may comprise the agent 1001 itself. This is illustrated in FIG. 10, which depicts a cross-sectional view of a polymer shell 1002 having cavities 1003, shaped to receive and resiliently reposition teeth, and an agent 1001 attached to its surface. It may be appreciated that the depictions of the agent is for illustration purposes and does not necessarily reflect the actual shape, size relationship or distribution of the agent particles. This applies to all depictions of agents hereinafter. Such attachment or formation of the layer may be achieved by applying the agent 1001 to the surface of the shell 1002 by a number of methods, including spraying, painting and/or dipping. Thus, when the oral delivery appliance 1000 is placed over the patient's teeth, the agent may then be released to the oral environment. When the agent 1001 is attached to the inside surface of the appliance 1000, as shown in FIG. 10, the agent may directly contact the teeth and/or gingiva. This may be best suited for treatments such as fluoride or antibiotic therapy which benefit from direct contact with the teeth and/or gingiva. However, other treatments, such as breath freshening, may most benefit from attachment to the outer surface of the appliance 1000. Therefore, agents 1001 may be attached to any or all surfaces of the appliance 1000.

Figure 11:
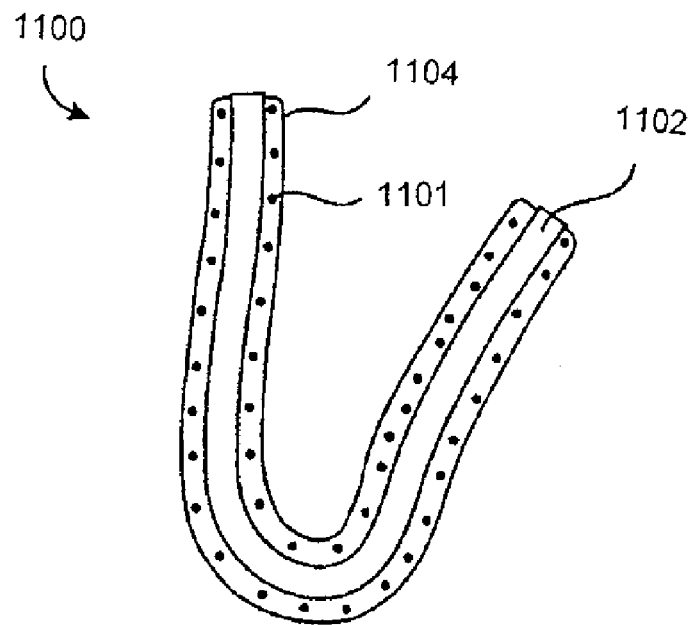
FIG. 11 is a cross-sectional view of an appliance having a semisolid material containing an agent applied to its surface.
Figure 12:
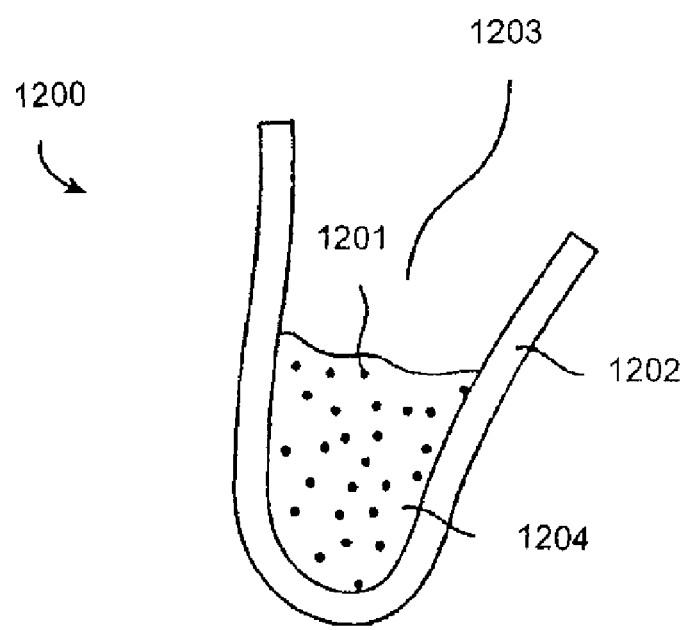
FIG. 12 is a cross-sectional view of an appliance having a cavity filled with a semisolid material containing an agent.

In another embodiment the appliance 1100 can include a layer that comprises the agent 1001 present in a carrier or binder. A common carrier for suspension of an agent is a semisolid material, such as a gel, jelly or putty. As depicted in FIG. 11, such semisolid material 1104 may be applied to the surface of the shell 1102 by spraying, painting and/or dipping to form a coating or film. Alternatively, as depicted in FIG. 12, the semisolid material 1204 may be deposited in the cavities 1203 of the polymer shell 1202 which are shaped to receive the teeth. The cavities 1203 may be filled to any desired level such that when the appliance 1200 is positioned over the teeth, the teeth will directly contact the material 1204 and displace any extra material 1204. Delivery of an agent 1201 by the use of such a material 1204 is most common in bleaching and fluoride treatments, however any type of agent 1201 may be used.

Another type of layer is a controlled-release material impregnated with the agent, wherein the rate controlling material controls the rate at which the agent is released from the layer. Controlled-release or rate-controlled materials deliver an agent at a predetermined rate. As previously described, such delivery may be achieved by a number of methods. First, the agent may be released by diffusion through the controlled-release material. In this case, the agent is typically present as finely dispersed particles in a polymer matrix membrane. This is often termed a monolithic dispersed type system, monolithic device, or matrix diffusion system. As the concentration of agent is reduced in the matrix due to diffusion delivery to the oral environment, the slope of the drug diffusion curve is also reduced. The agent delivery rate decreases over time as the material is depleted. Hence, the characteristic release profile of a monolithic system follows an asymptotic curve; after an initial burst of rapid release, the elution approaches a constant rate. Second, the agent may be released by degradation of the controlled-release material. Degradation may be achieved by a number of mechanisms, including enzymatic degradation by enzymes in the saliva. The agent may be encapsulated or contained in a biodegradable material, such as a polymer matrix. Any number of degradation rates may be achieved by manipulating the molar ratio of the monomers in the matrix. Further, the agent may be released by a combination of diffusion and degradation of the releasing layer. Alternatively or in addition, the agent may be released by elution from pores within the releasing layer. Depending on the structure of the layer, elution from the pores may be achieved by a number of methods. If the agent is contained in a controlled-release material which fills the pores, the agent may be released from the controlled-release material by diffusion and/or degradation and then elution from the pores themselves.

Figure 13:
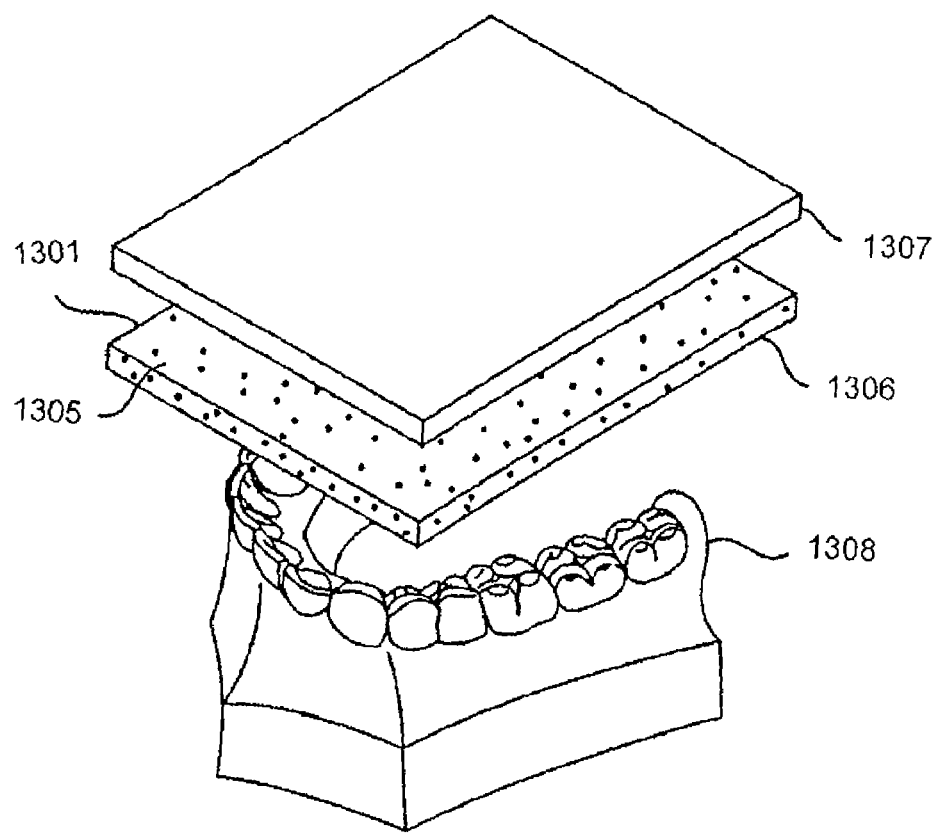
FIG. 13 illustrates the layering of a sheet of controlled-release material containing an agent with a polymeric sheet for use in the formation of an oral delivery appliance.

One attribute of controlled-release materials is that they may be provided in a solid form, such as a thin film or sheet, which may be attached to the polymeric shell of an elastic repositioning appliance. Referring to FIG. 13, a controlled-release material 1305 containing the agent 1301 may be provided as a sheet 1306 and used in the formation of an appliance of the present invention. Here, the sheet 1306 may be layered with an elastomeric polymer sheet 1307 over a mold 1308 of the patient's dentition. Together the sheets 1306, 1307 may be vacuum formed over the mold 1308 to form the repositioning appliance. By placing the controlled-release material sheet 1306 between the mold 1308 and the polymer sheet 1307, as shown, the controlled-release material 1305 will cover the inside surfaces of the appliance and will be positioned against the patient's teeth and/or gums when the appliance is in place. This may be most beneficial for elution of agents 1301 such as fluoride, antibiotics or bleaching materials.

Figure 14:
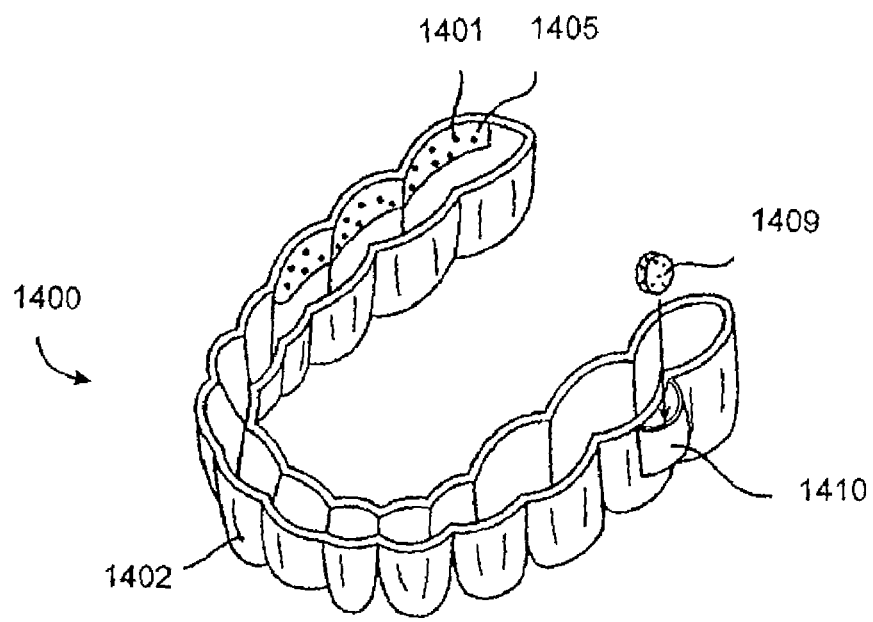
FIG. 14 illustrates the attachment of a controlled-release material to the polymeric shell of an appliance and the insertion of a controlled-release tablet into a portion of the polymeric shell.

Alternatively, the controlled-release material 1405 may be attached to the polymeric shell 1402 of the oral delivery appliance 1400 after forming the appliance. As shown in FIG. 14, the controlled-release material 1405 containing the agent 1401 may be laminated, bonded or otherwise attached to a surface of the polymer shell 1402 in a desired area. Such attachment may be removable, so that the material 1405 may be removed when the agent 1401 has substantially eluted or the therapy is to be discontinued, or it may be non-removable, so that the material 1405 is present throughout the life of the appliance. Also shown in FIG. 14 is the use of a controlled-release tablet 1409 which may be inserted into a pocket 1410 or portion of the polymeric shell 1402 of the appliance 1400. Portions of the pocket may be perforated or meshed to facilitate delivery of the agent. The agent may then elute from the tablet 1409 into the oral environment over time. This design may be most applicable to elution by degradation of the tablet 1409, wherein the tablet 1409 may be replaced periodically for renewed delivery.

In a further embodiment, the releasing means comprises a reservoir formed in the polymer shell in addition to the cavity which receives the teeth. Reservoir devices or membrane diffusion systems can supply an agent or substance at a constant rate under sink conditions. These systems consist of three elements: a reservoir containing the agent, a low concentration sink, such as the oral environment, and a rate-controlling membrane separating the reservoir from the sink. The system obeys Fick's Law of Diffusion for the mass flux across the membrane. Thus, the system is held at a constant delivery rate based on the diffusion coefficient through the membrane.

Figure 15:
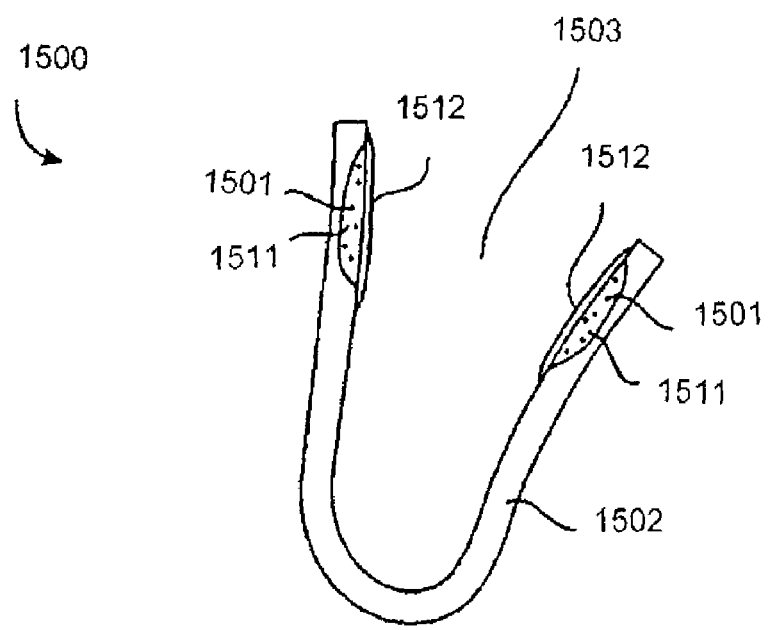
FIG. 15 illustrates a reservoir type releasing means having sealed ends.
Figure 16:
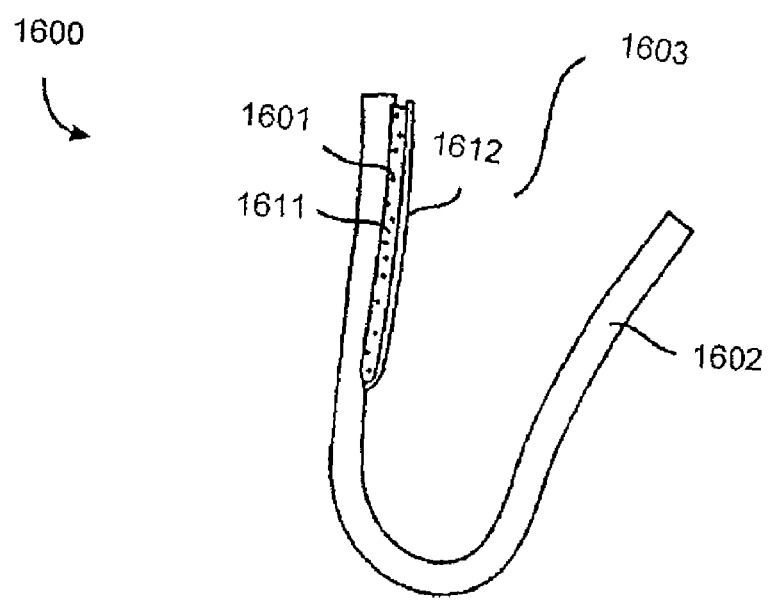
FIG. 16 illustrates a reservoir type releasing means that is accessible to the user so that the reservoir may be replenished with an agent.

Referring to FIG. 15, the releasing means is shown to comprise a reservoir 1511 formed in the polymer shell 1502, in addition to the cavity 1503 which receives the teeth. The reservoir holds the agent 1501 and is covered by a rate controlling membrane 1512 which controls the rate at which the agent 1501 is released from the reservoir 1511. The reservoirs 1511 are depicted as being located substantially within the wall of the polymer shell 1502 for elution to the cavity 1503. However, it may be appreciated that reservoirs 1511 may be located anywhere in the shell 1502, may be external to the wall of the shell 1502 and may elute in any direction. The reservoirs 1511 may be pre-filled with the agent 1501 to be released. That is, the appliance 1500 is provided with the reservoirs 1511 filled with the agent 1501. In this case, the reservoirs 1511 may be sealed by the membrane 1512 as depicted in FIG. 15. However, the appliance 1600 can include a reservoir 1611 formed in the polymer shell 1602, in addition to the cavity 1603 which receives the teeth. The reservoirs 1611 may also be accessible to the user so that the reservoir may be replenished with agent 1601 as desired. In this case, the reservoir 1611 may be not be sealed by the membrane 1612 as depicted in FIG. 16.

Figure 17:
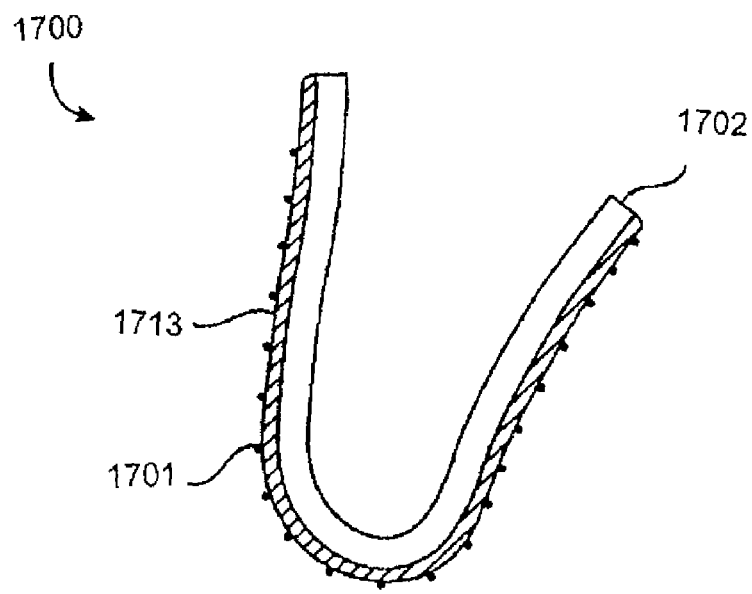
FIG. 17 is a cross-sectional view of an appliance having a binding material and releasably bound agent applied to its surface.

In another embodiment, the agent 1701 is supported by a carrier. As depicted in FIG. 17, the carrier comprises a binding material 1713 which releasably binds the agent 1701 to a surface of the polymeric shell 1702 of the appliance 1700. The binding material 1713 may release the agent 1701 by a number of mechanisms, including dissolution of the binding material 1713, activation or deactivation of the binding material 1713 or any other release mechanism.

Figure 18:
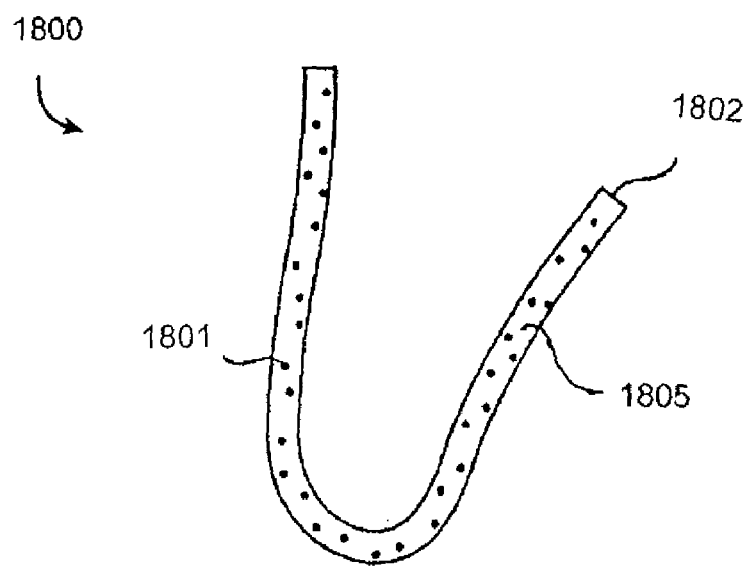
FIG. 18 is a cross-sectional view of an appliance comprised of a controlled-release material containing an agent.

In a further embodiment, as depicted in FIG. 18, the polymeric shell 1802 of the oral delivery appliance 1800 is comprised of a controlled-release material 1805 containing an agent 1801. In this case, the controlled-release material 1805 itself is formed to function as a repositioning appliance. This may be achieved by vacuum forming a sheet of controlled-release material over a mold of the patient's teeth. The agent 1801 may then elute from the appliance 1800 by means of diffusion or other release mechanisms.

Means for releasing the agent to the oral environment have been described in a number of embodiments, above, in regards to the agent itself. However, in each embodiment, the agent may first be encapsulated or microencapsulated in a material, typically a polymer. Such encapsulation may be desired or necessary to protect the agent from the effects of processing. For example, some agents may be hydrolyzed or denatured by processes such as extrusion or thermoforming which may be involved in the production of the appliance. Encapsulation may also protect the agent from environmental factors throughout the shelf-life of the appliance. Therefore, in the above descriptions and throughout, "agent" may identify the agent itself or an encapsulated agent.

Agents may be encapsulated or entrapped by a number of materials. Such materials may include polylactic acids, polycapric lactones, polyvinyl alcohols, polyacrylic acids, polyethylene oxides, polylactide glycolic biodegradable polymer capsules and side-chain crystallizable polymers, to name a few. Encapsulation may be achieved by a variety of processes. Particularly, the agent may be encapsulated by spray-drying. For example, the agent may be mixed or combined with a solvent, such as polyvinyl alcohol, and then combined with a polymer resin. After the solvent evaporates, polymer microcapsules, each containing the agent dispersed throughout its matrix, are retained.

The encapsulating or entrapping material may or may not provide controlled-release of the agent from the microsphere. If the encapsulating material does provide controlled-release capabilities, such a layer would be in addition to any controlled-release means for releasing the agent previously described. For example, the encapsulated agent may be dispersed throughout a sheet of controlled-release material which is later attached to the polymeric shell of an elastic repositioning appliance. When the appliance is positioned in the patient's mouth, the agent may elute at a controlled rate based on the release of the agent from the encapsulating material and from the sheet of controlled-release material.

Similarly, the encapsulating material may be an ion exchange resin. Such resins have a very high surface area and are able to absorb a large quantity of an agent for controlled-delivery. An exemplary resin is sold under the trademark MICROSPONGE (Advanced Polymer Systems), and described, for example, in U.S. Pat. No. 5,145,675, the full disclosure of which is incorporated herein by reference. In addition to serving as an encapsulating material, ion exchange resins may be used for as a controlled-delivery material in any of the above described embodiments.

Figure 19:
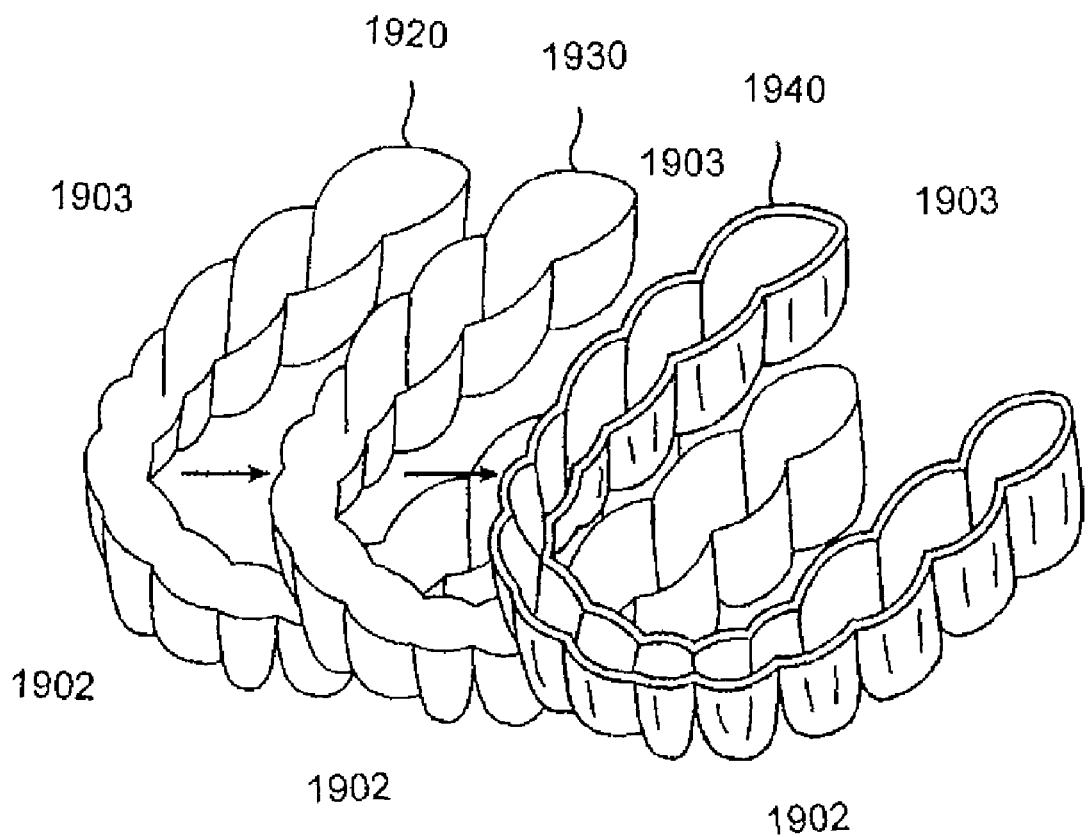
FIG. 19 illustrates a gradual color change of an appliance from transparent to colored as the appliance changes in temperature.

In some instances it may be desirable to change a visual characteristic of the polymeric shell of an oral appliance. Such appliances comprise a polymeric shell 1902 having a cavity 1903 shaped to be removably placeable over the teeth and a material on or within the shell that changes a visual characteristic of the shell. Such a change is typically in response to a change in the environment. For example, the material may be a dye which changes color when the appliance is removed from the patient's mouth and changes temperature due to the change in environment. This gradual color change is illustrated in FIG. 19. For example, as shown, a transparent oral delivery appliance 1920 will remain transparent when it is in the mouth and maintained at body temperature. Upon removal from the mouth, the appliance will cool to room temperature. As the appliance begins to cool, the colorant will gradually become visible, as illustrated in the tinted oral delivery appliance 1930. As the appliance equilibrates to room temperature, the colorant will become more visible, as illustrated in the colored oral delivery appliance 1940.

Figure 20:
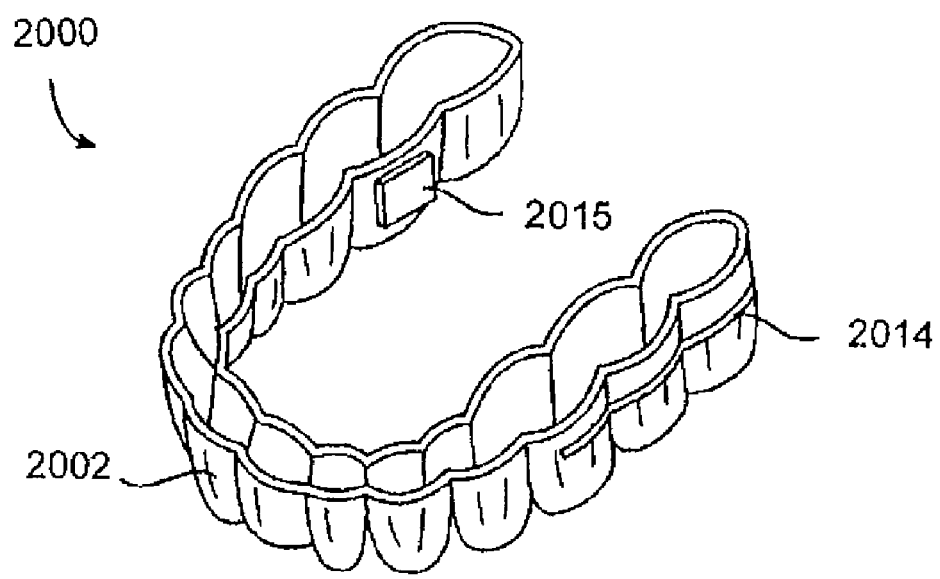
FIG. 20 depicts the use of a color or dye localized in a specific area; examples of a stripe formed in the appliance and a portion of colored material affixed to a surface are shown.

The color may be dispersed throughout the appliance, as in FIG. 19, or the color may be localized in a specific area within or on a surface of the appliance. As shown in FIG. 20, the appliance 2000 may contain, for example, a stripe 2014 of color or dye in a specific location. Such a stripe 2014 may be visible at all times or it may only appear when removed from the oral environment. In either case, the stripe 2014 may be positioned so that it is hidden from view, i.e. along the lingual surfaces or along the molars, or it may be placed anywhere along the appliance. 2000. Likewise, a portion of material 2015 which changes a visual characteristic may be attached, bonded or laminated to a surface of the polymer shell 2002, either removably or permanently.

Portions of the system and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow. For example, although films or appliances have been disclosed as mechanisms for compliance measurement, droplets can be used to deliver the compliance indicating substances to the patient as well. Other embodiments for compliance indication can be used as well. Whereas particular embodiments of the present invention have been described herein for purposes of illustration, it will be evident to those skilled in the art that numerous variations of the details may be made without departing from the invention as defined in the appended claims.

What is claimed is:

1. An apparatus for monitoring orthodontic treatment compliance, the apparatus comprising:
a tooth repositioning appliance including one or more cavities adapted to be worn over one or more teeth, wherein the one or more cavities are shaped to receive and reposition the one or more teeth from one arrangement to a successive arrangement; and
an orthodontic treatment compliance indicator mounted on the tooth repositioning appliance to indicate compliance in wearing the tooth repositioning appliance by demonstrating a change in at least one characteristic of the indicator, wherein the change is a color change of the indicator and occurs due to a reaction between one or more materials in the indicator and one or more oral fluids.

2. The apparatus of claim 1, wherein the tooth repositioning appliance is used in conjunction with treatment for a predetermined period of time.

3. The apparatus of claim 1, wherein the compliance is visually and chemically indicated.

4. The apparatus of claim 1 wherein the color change is affected by at least one of: moisture, temperature, one or more chemicals, and one or more biological substances.

5. The apparatus of claim 1, wherein the color change is detectable by human or machine vision.

6. The apparatus of claim 1, wherein the color change is affected by a degradation of a biodegradable or a dissolvable polymer.

7. The apparatus of claim 1, wherein the compliance is indicated by exposure of the indicator previously hidden under a polymeric layer of the tooth repositioning appliance.

8. The apparatus of claim 7, wherein the color change occurs after degradation or dissolution of the polymeric layer.

9. The apparatus of claim 1, wherein the indicator collects oral fluids.

10. The apparatus of claim 9, wherein compliance is indicated by a concentration change of ingredients in oral fluids.

11. The apparatus of claim 1, wherein the reaction is a chemical reaction through a semi-permeable membrane.

12. The apparatus of claim 1, wherein the indicator includes one or more conducting fillers.

13. The apparatus of claim 1, wherein the reaction is affected by a mass transfer or a chemical reaction.

14. The apparatus of claim 1, wherein compliance is determined by use of the tooth repositioning appliance over the teeth for a prolonged period of time.

15. The apparatus of claim 1, wherein the tooth repositioning appliance is configured to adjust a configuration of the teeth.

16. An apparatus for monitoring orthodontic treatment compliance, the apparatus comprising:
a tooth repositioning appliance including one or more cavities adapted to be worn over one or more teeth, wherein the one or more cavities are shaped to receive and reposition the one or more teeth from one arrangement to a successive arrangement; and
an orthodontic treatment compliance indicator mounted on the tooth repositioning appliance to indicate compliance in wearing the tooth repositioning appliance by demonstrating a change in at least one characteristic of the indicator, wherein the change is a color change of the indicator and occurs due to a reaction between one or more materials in the indicator and one or more oral fluids.

* * * * *